(12) United States Patent
Nagatomi et al.

(10) Patent No.: US 10,101,272 B2
(45) Date of Patent: Oct. 16, 2018

(54) SAMPLE DETECTION PLATE, AND FLUORESCENCE DETECTION SYSTEM AND FLUORESCENCE DETECTION METHOD USING SAME

(71) Applicant: PANASONIC INTELLECTUAL PROPERTY MANAGEMENT CO., LTD., Osaka (JP)

(72) Inventors: Kenji Nagatomi, Osaka (JP); Masaya Nakatani, Hyogo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 171 days.

(21) Appl. No.: 15/226,368

(22) Filed: Aug. 2, 2016

(65) Prior Publication Data

US 2016/0341665 A1    Nov. 24, 2016

Related U.S. Application Data

(63) Continuation of application No. PCT/JP2015/000416, filed on Jan. 30, 2015.

(30) Foreign Application Priority Data

Feb. 4, 2014 (JP) ................ 2014-019047

(51) Int. Cl.
*G02B 21/00* (2006.01)
*G01N 21/64* (2006.01)
(Continued)

(52) U.S. Cl.
CPC ......... *G01N 21/6428* (2013.01); *G01N 21/64* (2013.01); *G01N 21/6458* (2013.01);
(Continued)

(58) Field of Classification Search
None
See application file for complete search history.

(56) References Cited

U.S. PATENT DOCUMENTS 6,027,695 A * 2/2000 Oldenburg ............ B01L 3/5085
422/504
7,429,479 B2 * 9/2008 Harding ................ B01L 3/5027
356/246
(Continued)

FOREIGN PATENT DOCUMENTS

EP    1 333 286 A1    8/2003
JP    2002-291499 A   10/2002
(Continued)

OTHER PUBLICATIONS

International Search Report and Written Opinion, issued in corresponding International Patent Application No. PCT/JP2015/000416, dated Apr. 21, 2015; with partial English translation.
(Continued)

*Primary Examiner* — Yara B Green
(74) *Attorney, Agent, or Firm* — McDermott Will & Emery LLP

(57) ABSTRACT

A sample detection plate according to the present disclosure includes a first substrate having a first surface, and a sample container that is provided on the first surface of the first substrate to contain a sample that absorbs electromagnetic waves having a predetermined wavelength. The first substrate includes a first material that emits autofluorescence in response to the electromagnetic waves having the predetermined wavelength.

10 Claims, 7 Drawing Sheets

(51) Int. Cl.
    *G02B 21/34* (2006.01)
    *G01N 21/03* (2006.01)
(52) U.S. Cl.
    CPC ..... *G02B 21/34* (2013.01); *G01N 2021/0339* (2013.01); *G01N 2021/6439* (2013.01)

(56) References Cited

U.S. PATENT DOCUMENTS

| | | | | |
|---|---|---|---|---|
| 2005/0009060 | A1* | 1/2005 | Beernink | G01N 15/1459 435/6.14 |
| 2005/0285040 | A1* | 12/2005 | Fukui | G01J 5/34 250/338.3 |
| 2005/0287040 | A1* | 12/2005 | Giebeler | B01L 3/5085 422/82.08 |
| 2005/0287041 | A1* | 12/2005 | Martin | G01J 3/22 422/83 |
| 2006/0160129 | A1* | 7/2006 | Zauderer | C12N 15/1034 435/6.14 |
| 2009/0088335 | A1* | 4/2009 | Strom | C12Q 1/6869 506/9 |
| 2009/0159815 | A1 | 6/2009 | Kinoshita et al. | |
| 2010/0248993 | A1* | 9/2010 | Tserepi | B01J 19/0046 506/30 |
| 2010/0273168 | A1* | 10/2010 | Krockenberger | G01N 15/00 435/6.12 |
| 2013/0004976 | A1* | 1/2013 | Shimizu | G01N 33/74 435/7.94 |
| 2013/0065795 | A1* | 3/2013 | Allbritton | C12M 23/12 506/26 |
| 2013/0107256 | A1* | 5/2013 | Mitsuyama | G01N 15/1012 356/343 |
| 2014/0356969 | A1 | 12/2014 | Nishikawa et al. | |

FOREIGN PATENT DOCUMENTS

| | | |
|---|---|---|
| JP | 2006-018394 A | 1/2006 |
| JP | 2006-214956 A | 8/2006 |
| JP | 2006-266768 A | 10/2006 |
| JP | 2009-151022 A | 7/2009 |
| WO | 2013/157283 A1 | 10/2013 |

OTHER PUBLICATIONS

Extended European Search Report issued in corresponding European Patent Application No. 15746094.0, dated Dec. 22, 2016.

* cited by examiner

SAMPLE DETECTION PLATE, AND FLUORESCENCE DETECTION SYSTEM AND FLUORESCENCE DETECTION METHOD USING SAME

CROSS REFERENCE TO RELATED APPLICATION

This application is a U.S. continuation application of PCT International Patent Application Number PCT/JP2015/000416 filed on Jan. 30, 2015, claiming the benefit of priority of Japanese Patent Application Number 2014-019047 filed on Feb. 4, 2014, the entire contents of which are hereby incorporated by reference.

BACKGROUND OF THE INVENTION

1. Technical Field

The present disclosure relates to a sample detection plate used in a fluorescence detection system for sample observation, and the fluorescence detection system and a fluorescence detection method using the sample detection plate.

2. Description of the Related Art

Particularly in the field of medicine such as those at clinical sites, it is important to detect from among a large number of cells a cell infected with pathogens or a cell having a predetermined condition. Methods for detecting a cell having a predetermined condition include, for example, a method of fluorescently-labeling a specific protein or nucleus with fluorochrome, and observing the protein or nucleus using a microscope including a fluorescent observation optical system.

In the case of calculating an infection rate of the observed cells, the number of cells within a field of view is counted. In order to count the number of the cells, an outer shape of each cell is detected so as to distinguish between an inside and an outside of the cell. Known methods for identifying the outer shape of the cell include, for example, a method of using a phase contrast image captured by a phase contrast observation optical system. Furthermore, a method of using a fluorescent image captured by a fluorescent observation optical system is known for observing fluorescently-labeled cells.

For example, Japanese Unexamined Patent Application Publication No. 2006-18394 is known as a related art document pertinent to the disclosure of the present application.

SUMMARY

As described above, determining the infection rate of cells with bacteria or the like involves the detection of the outer shape of the cells and the detection of the fluorescently-labeled cells within an observation area. In a conventional detection method, a microscope including the phase contrast observation optical system is used for detecting the outer shape of the cells. Also, a microscope including the fluorescent observation optical system is used for detecting the fluorescently-labeled cells. Accordingly, the detection of the outer shape of the cells and the detection of the fluorescently-labeled cells necessitate the phase contrast observation optical system as well as the fluorescent observation optical system.

The present disclosure solves the problem mentioned above, and aims to provide a sample detection plate that makes it possible to detect the outer shape of a sample in a detection device that includes a fluorescent optical system and need not include a phase contrast observation optical system, and a fluorescence detection system and a fluorescence detection method using the sample detection plate.

Solution to Problem

In order to achieve the above, a sample detection plate disclosed herein includes a first substrate having a first surface, and a sample container that is provided on the first surface of the first substrate to contain a sample that absorbs electromagnetic waves having a predetermined wavelength. The first substrate includes a first material that emits autofluorescence in response to the electromagnetic waves having the predetermined wavelength.

The sample detection plate disclosed herein allows detection of autofluorescence emitted by a substrate in response to electromagnetic waves having a predetermined wavelength with which the sample detection plate is irradiated, using a detection device including the fluorescent optical system. In this way, it is possible to detect the outer shape of the sample without using the phase contrast observation optical system.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENT

Referring to FIG. 1 to FIG. 7, a sample detection plate in an embodiment of the present disclosure will be described.

Figure 1:
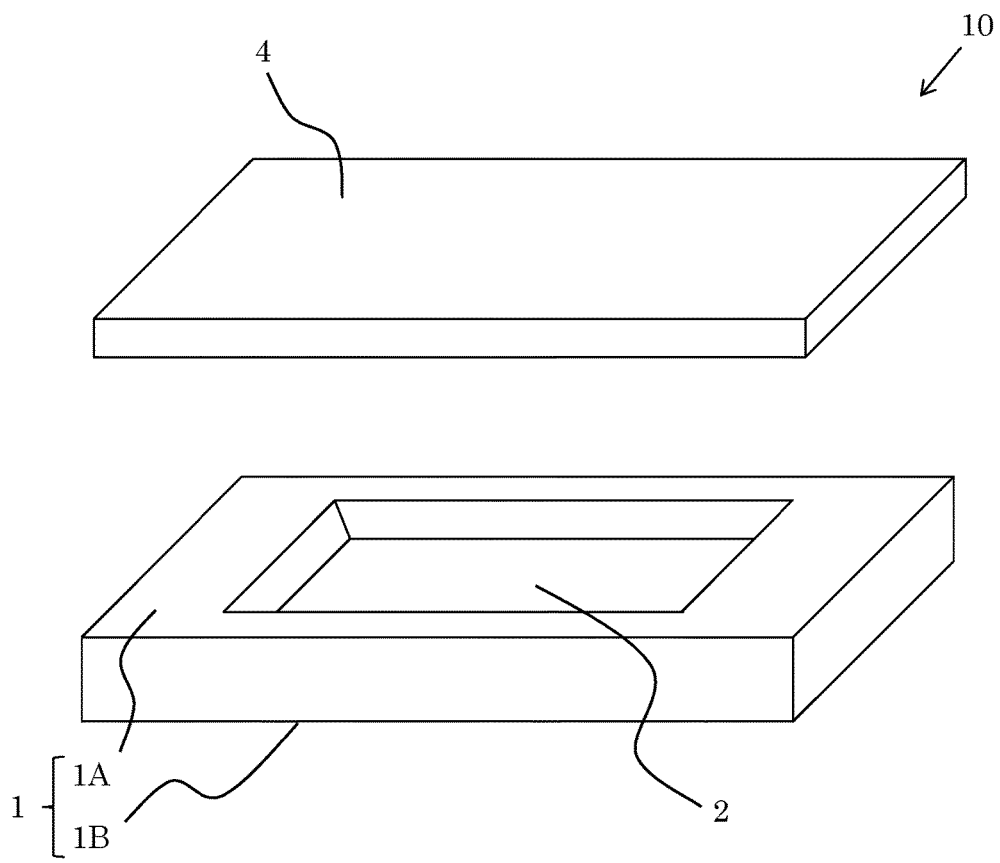
FIG. 1 is an exploded perspective view schematically illustrating a sample detection plate according to an embodiment of the present disclosure.
Figure 2:
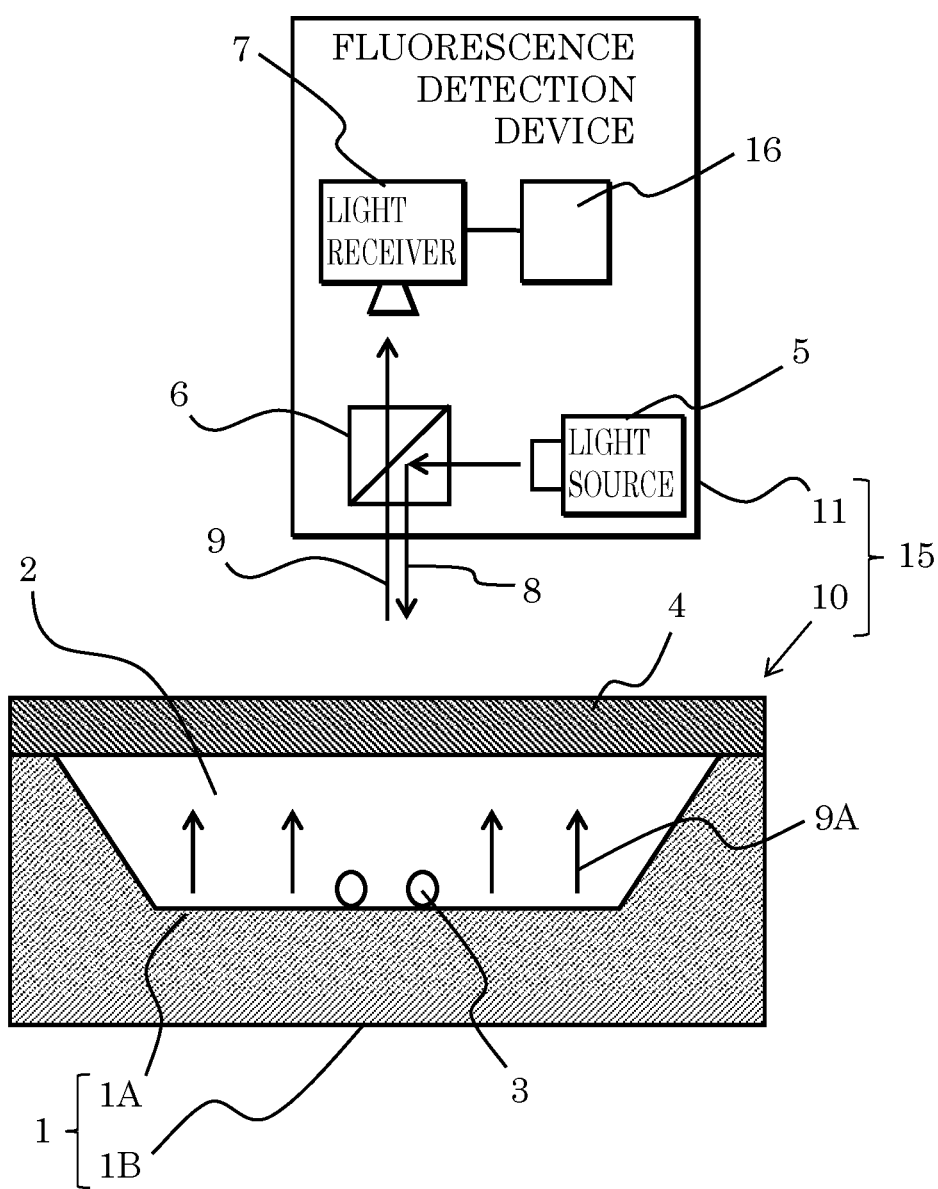
FIG. 2 is a schematic view illustrating a fluorescence detection system according to an embodiment of the present disclosure.

FIG. 1 is an exploded perspective view schematically illustrating a configuration of sample detection plate 10. FIG. 2 is a schematic view illustrating a configuration of fluorescence detection system 15. FIG. 2 shows a cross-section of sample detection plate 10.

Sample detection plate 10 is provided in, for example, a detection device including a fluorescent optical system and used for detecting an outer shape of a sample.

The fluorescent optical system is a group of configurations that are included in the detection device and needed for detecting fluorescence emitted by an object. The fluorescent optical system is configured by a combination of a part or a whole of a light source, a lens, a mirror and a light receiver included in the detection device, for example.

Fluorescence detection system 15 includes sample detection plate 10 and fluorescence detection device 11.

Sample detection plate 10 includes first substrate 1 having first surface 1A and second surface 1B facing away from first surface 1A, and sample container 2 that is provided on first surface 1A of first substrate 1 to contain sample 3 that absorbs electromagnetic waves 8 having a predetermined wavelength. First substrate 1 is formed of a first material that emits autofluorescence 9A in response to electromagnetic waves having a predetermined wavelength. Furthermore, sample detection plate 10 includes second substrate 4 facing first surface 1A. Sample container 2 is sandwiched between first substrate 1 and second substrate 4.

With the above configuration, the detection device including the fluorescent optical system detects autofluorescence 9A emitted by first substrate 1 in response to electromagnetic waves 8 with which sample detection plate 10 is irradiated, thereby easily detecting an outer shape of sample 3 without using a phase contrast optical system. Sample 3 may be, for example, cells or biological tissues.

In the following description, first surface 1A of first substrate 1 is referred to as an upper surface, and second surface 1B of first substrate 1 is referred to as a lower surface.

First substrate 1 is formed of a first material that emits autofluorescence 9A in response to electromagnetic waves 8 having a predetermined wavelength. Fluorescence detection system 15 receives autofluorescence 9A shown by sample detection plate 10 in response to electromagnetic waves 8, and detects the outer shape of sample 3. Thus, it is beneficial that the intensity of autofluorescence 9A emitted by first substrate 1 in response to electromagnetic waves 8 should be relatively high. As the intensity of autofluorescence 9A emitted by first substrate 1 rises, fluorescence detection system 15 can obtain an image with a sharper outline of sample 3.

Consequently, the first material for first substrate 1 may be a material in which the intensity of autofluorescence emitted by first substrate 1 in response to electromagnetic waves 8 having a predetermined wavelength is greater than the intensity of autofluorescence of glass. The first material may be, for example, a resin material such as polycarbonate, polystyrene, cycloolefin copolymer, acrylic, or dimethylpolysiloxane. In particular, polycarbonate emits autofluorescence 9A that has a great intensity in response to electromagnetic waves 8 having a predetermined wavelength. Thus, it is desirable that first substrate 1 should contain polycarbonate. Moreover, the intensity of autofluorescence 9A is adjustable by changing the thickness of first substrate 1, the content of the first material in first substrate 1, and so on other than the material of first substrate 1.

The shape of first substrate 1 can be freely selected from among a square, a rectangle, a disc shape, etc., for example, according to the configuration of the detection device.

Sample container 2 is provided on an upper surface side of first substrate 1, and contains sample 3 that absorbs electromagnetic waves 8 having a predetermined wavelength. In FIG. 1, sample container 2 is formed of one region located on the upper surface of first substrate 1. For example, sample container 2 can be formed of a recess etched into first substrate 1. Also, first substrate 1 may be formed of a sample containing layer attached to a flat plate. The sample containing layer has a through hole, for example. In this case, sample container 2 is a recess formed of the through hole of the sample containing layer and the flat plate.

The size, depth, and number of sample container 2 or sample containers 2 are determined depending on the size of the sample, the size of light source 5 and light receiver 7 of the detection device, etc. The number of samples 3 to be contained in sample container 2 is adjustable by presetting the size and depth of sample container 2.

It is beneficial that samples 3 should be contained flat as a single layer on a bottom surface of sample container 2. When samples 3 are contained in a stacked manner inside sample container 2, it becomes difficult to identify the shape of the samples at the time of detection.

Furthermore, sample detection plate 10 includes second substrate 4. Second substrate 4 has a function as a lid that is provided so as to cover sample container 2. By providing second substrate 4, it becomes possible to prevent sample 3 contained in sample container 2 from being scattered away from sample container 2 during detection operation. It should be noted that second substrate 4 does not have to be provided as long as the sample in sample container 2 is not scattered. Moreover, as sample container 2, a recess may be provided in second substrate 4 or both of first substrate 1 and second substrate 4.

Fluorescence detection device 11 has the fluorescent optical system. The fluorescent optical system includes light source 5, mirror 6, and light receiver 7. Light source 5 emits electromagnetic waves 8 having a predetermined wavelength. Electromagnetic waves 8 may be, for example, excitation light such as laser light. Mirror 6 reflects, toward sample detection plate 10, electromagnetic waves 8 emitted from light source 5. Furthermore, mirror 6 transmits fluorescence 9 emitted from sample detection plate 10. Light receiver 7 receives fluorescence 9 that has been transmitted by mirror 6. Moreover, image generator 16 for generating an image using fluorescence 9 that has been received may be provided.

Fluorescence detection system 15 detects, from above the upper surface of first substrate 1, autofluorescence 9A emitted by first substrate 1 in response to electromagnetic waves 8 having a predetermined wavelength. Light receiver 7 that receives autofluorescence 9A emitted by sample detection plate 10 is disposed above the upper surface of first substrate 1. Furthermore, light source 5 that emits electromagnetic waves 8 is disposed above the upper surface of first substrate 1 similarly to light receiver 7.

Sample detection plate 10 is irradiated with electromagnetic waves 8 from light source 5 disposed on the upper surface side of first substrate 1. First substrate 1 is formed of a first material that emits autofluorescence 9A in response to electromagnetic waves 8. Thus, first substrate 1 emits autofluorescence 9A when irradiated with electromagnetic waves 8. Autofluorescence 9A emitted by first substrate 1 is received by light receiver 7 disposed on the upper surface side of sample detection plate 10. Additionally, sample 3 to be contained in sample container 2 absorbs a part of electromagnetic waves 8 with which sample detection plate 10 is irradiated.

It should be noted that a position of light source 5 for emitting electromagnetic waves 8 is not limited to the upper surface side of first substrate 1. Light source 5 may be disposed on a lower surface side or a lateral surface side of first substrate 1, for example. However, in the case where electromagnetic waves 8 directly enter light receiver 7, the background brightness of a fluorescent observation image may increase. In this case, it is beneficial that a wavelengthselective optical filter or the like for reducing electromagnetic waves 8 should be further provided in light receiver 7.

Figure 3:
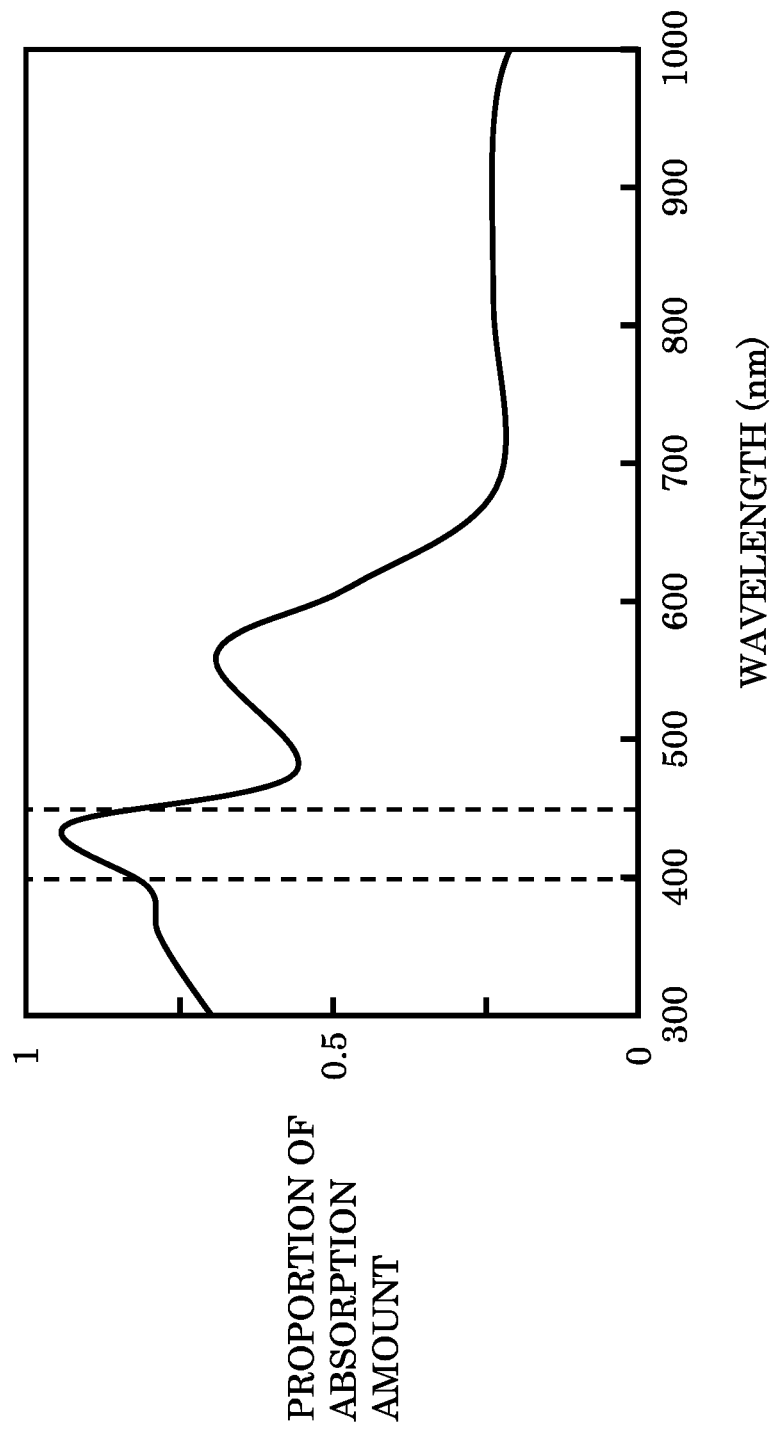
FIG. 3 is a graph showing an electromagnetic wave absorption spectrum of hemoglobin.

Electromagnetic waves 8 having a predetermined wavelength are determined depending on an absorption wavelength spectrum of sample 3. Sample 3 that absorbs electromagnetic waves 8 having a predetermined wavelength may be, for example, a red blood cell. FIG. 3 is a graph showing an absorption wavelength spectrum of hemoglobin contained in a red blood cell. Hemoglobin contained in a red blood cell strongly absorbs electromagnetic waves in a wavelength band of especially shorter than or equal to 450 nm. On the other hand, in a wavelength band of shorter than or equal to 400 nm including an ultraviolet range, such electromagnetic waves may damage a biomaterial. Accordingly, in the case where sample 3 to be contained in sample container 2 is a red blood cell, it is appropriate that the above-noted electromagnetic waves having a predetermined wavelength should be electromagnetic waves having a wavelength ranging from 400 nm to 450 nm. Also, the sample is not necessarily limited to the red blood cell but may be a plant cell having chlorophyll, for example. In this case, since chlorophyll has an absorption wavelength band ranging approximately from 400 nm to 450 nm, it is appropriate that the above-noted electromagnetic waves having a predetermined wavelength should have a wavelength ranging approximately from 400 nm to 450 nm similarly to the red blood cell mentioned above. It is noted that electromagnetic waves absorbed by sample 3 are not limited to electromagnetic waves 8 emitted by the light source. For example, sample 3 may absorb autofluorescence 9A emitted by first substrate 1. In this case, the above-noted electromagnetic waves having a predetermined wavelength mean autofluorescence 9A.

In fluorescence detection system 15, it is beneficial that the second material forming second substrate 4 should be a material that does not emit autofluorescence in response to electromagnetic waves having a predetermined wavelength or a material that emits autofluorescence having a less intensity than an intensity of the autofluorescence emitted by first substrate 1 in response to electromagnetic waves having a predetermined wavelength. Autofluorescence 9A emitted by first substrate 1 is transmitted by sample container 2 and second substrate 4 and received by light receiver 7. Thus, if the autofluorescence emitted by second substrate 4 has a greater intensity than an intensity of the autofluorescence emitted by first substrate 1 in response to electromagnetic waves having a predetermined wavelength, it brightens and blurs the outline of sample 3 detected through the autofluorescence emitted by first substrate 1, making it difficult to detect the outer shape of sample 3. Accordingly, the second material for second substrate 4 can be glass, resin, etc., for example. It is appropriate that the second material should be a transparent material. In the case where the resin is used as the second material, it is beneficial that second substrate 4 should be formed of a resin having a less autofluorescence intensity than the first material.

Figure 4:
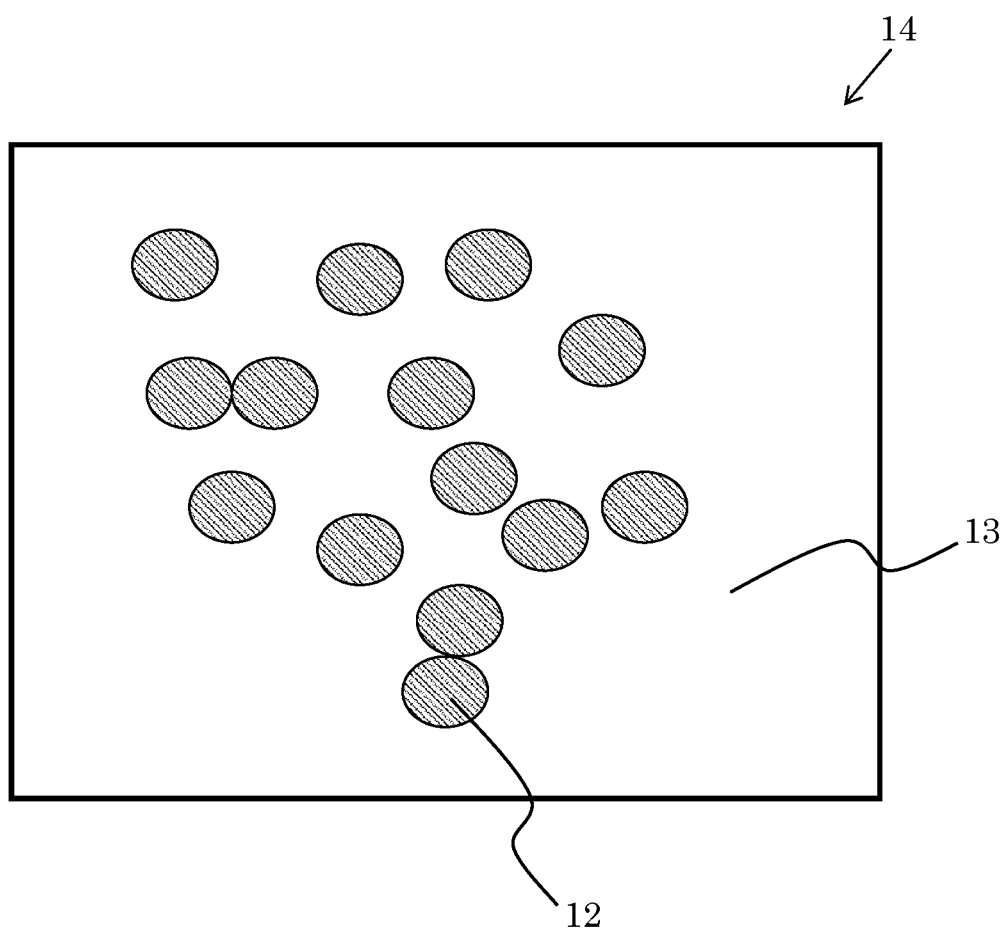
FIG. 4 schematically illustrates a fluorescent observation image in a sample container.

FIG. 4 schematically illustrates fluorescent observation image 14 in sample container 2. In fluorescent observation image 14, region 12 in which sample 3 is captured is detected to be dark. Region 13 in which sample 3 is not captured is detected to be bright. Since autofluorescence 9A emitted by first substrate 1 in response to electromagnetic waves 8 is received by light receiver 7 in region 13 where sample 3 is not captured, region 13 is imaged to be bright. In region 12 where sample 3 is captured, since sample 3 absorbs electromagnetic waves 8, the intensity of autofluorescence 9A that is emitted by first substrate 1 and received by light receiver 7 is less than that in region 13 where sample 3 is not captured. Thus, region 12 where sample 3 is captured is imaged as a dark part.

With such a configuration, autofluorescence 9A emitted by first substrate 1 in response to electromagnetic waves 8 with which sample detection plate 10 is irradiated is detected using fluorescence detection device 11 including the fluorescent optical system, so that the outer shape of the cell can be detected.

When counting the number of plural samples included in fluorescent observation image 14, the following method can be employed. First, the area of the dark part per sample is obtained. The area of the dark part per sample may be a known value, a value determined through work performed by an observer or a value determined by image processing. In the case where the area of the dark part per sample is determined through work performed by an observer or by image processing, an average per sample may be obtained from the total area of the dark parts of the plural samples and used as a representative value. Next, the area of the dark parts in fluorescent observation image 14 is determined by histogram or the like. Then, this area is divided by the area of the dark part per sample. The resultant value can be used as the count of samples 3. It should be noted that a threshold for extracting the dark parts is adjusted as necessary. In the case where sample 3 has a larger thickness in its central portion than its peripheral portion, fluorescent observation image 14 sometimes has the minimum brightness value in the central portion of sample 3. This is because an absorption amount of electromagnetic waves varies in sample 3. In this case, by searching for a point of the minimum brightness value using a peak analyzing technique in fluorescent observation image 14, it is also possible to count the number of samples 3. Incidentally, also in the case where contents are distributed at a high concentration in the central portion of sample 3, fluorescent observation image 14 sometimes shows the minimum brightness value for the similar reasons. In this case, it is also possible to count the number of samples 3 using the similar method.

Furthermore, although first substrate 1 that emits autofluorescence 9A in response to electromagnetic waves 8 having a predetermined wavelength has been provided as a single substrate in the above description, it may have a layered structure including a material that emits autofluorescence and a material that emits no autofluorescence. For example, similar effects can be obtained with a structure obtained by applying to a glass substrate a polycarbonate thin film that emits autofluorescence.

Now, a fluorescence detection method using sample detection plate 10 will be explained.

In the fluorescence detection method, sample detection plate 10 is prepared. Sample 3 is placed in sample detection plate 10. Electromagnetic waves 8 having a predetermined wavelength are passed through sample container 2 so that first substrate 1 is irradiated with electromagnetic waves 8 having a predetermined wavelength from a first surface side of first substrate 1. Autofluorescence 9A emitted by first substrate 1 in response to electromagnetic waves 8 is received from the first surface side of first substrate 1 through sample container 2. Using received autofluorescence 9A emitted by first substrate 1, an image is generated.

At the time of placing sample 3 in sample detection plate 10, sample 3 is stained with fluorochrome that emits fluorescence in response to electromagnetic waves 8 having a predetermined wavelength. For example, when the sample is a cell, a protein in a nucleus or a protein on a cell membrane is stained with the fluorochrome, thereby making it possible to also detect the fluorescence emitted by the fluorochrome using fluorescence detection device 11. At this time, it is possible to detect the outer shape of the cells through autofluorescence 9A by first substrate 1 and fluorescently detect nucleuses in the cells through the fluorescence emitted by the fluorochrome at the same time. It is appropriate that electromagnetic waves 8 that excite autofluorescence 9A emitted by first substrate 1 and electromagnetic waves 8 that excite the fluorescence emitted by the fluorochrome should be made to have substantially equal wavelengths. This allows fluorescence detection device 11 to detect the outer shape of the cells and fluorescently detect the nucleuses by the fluorochrome at the same time using one wavelength.

Furthermore, sample 3 may be placed in sample container 2 together with a solution containing fluorochrome. In this case, since the solution also emits fluorescence in response to electromagnetic waves 8, the difference in brightness between region 13 where sample 3 is not captured and region 12 where sample 3 is captured increases further, making it possible to distinguish the outer shape of sample 3 clearly. At this time, it is beneficial that the intensity of the fluorescence emitted by the fluorochrome contained in the solution should be greater than the intensity of autofluorescence 9A emitted by first substrate 1.

Moreover, in the generated image, a region where the fluorescence intensity is less than or equal to a predetermined threshold is determined to be a sample region, whereas a region where the fluorescence intensity is greater than the predetermined threshold is determined to be a background region. The sample region indicates region 12 where the sample is captured. The background region indicates region 13 where the sample is not captured.

Figure 5:
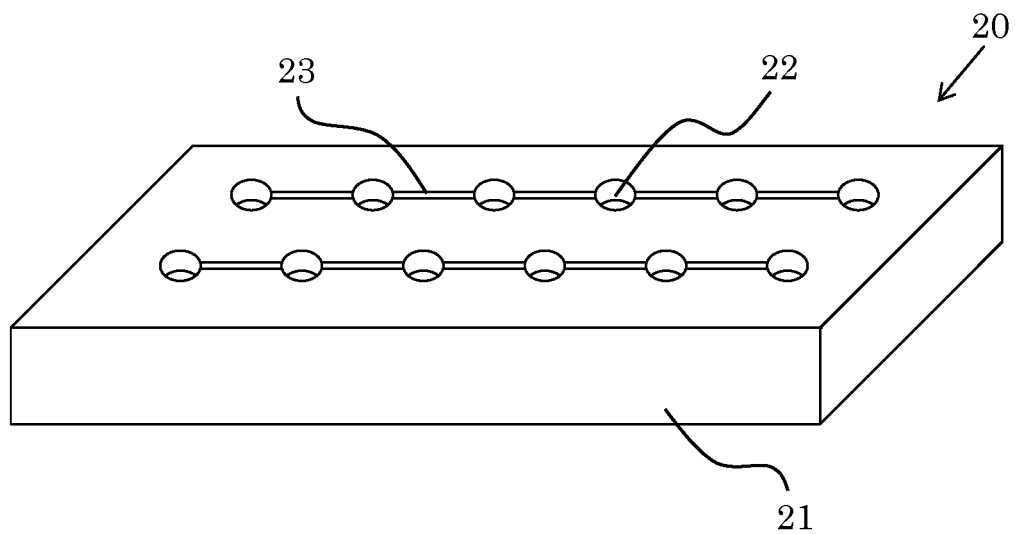
FIG. 5 is a top perspective view schematically illustrating another sample detection plate in an embodiment of the present disclosure.

FIG. 5 is a top perspective view schematically illustrating sample detection plate 20 in Variation 1. Sample detection plate 20 has a configuration in which a plurality of sample containers 22 are provided on substrate 21. Channel 23 for allowing the sample to travel between the plurality of sample containers 22 is provided on substrate 21. With channel 23, sample detection plate 20 can easily introduce the sample to sample containers 22. Substrate 21 contains a first material that emits autofluorescence in response to electromagnetic waves having a predetermined wavelength.

Figure 6:
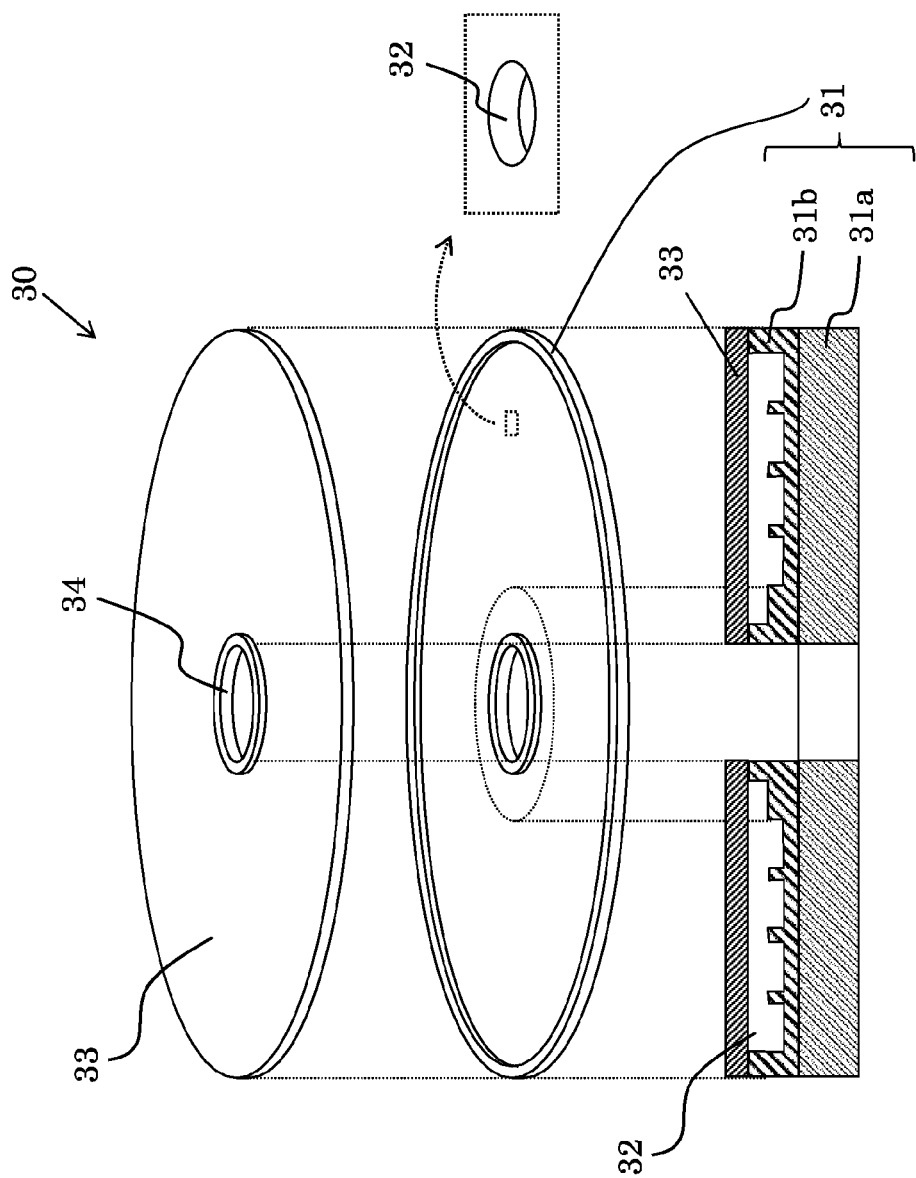
FIG. 6 is a view including a top perspective view and a sectional view schematically illustrating another sample detection plate in an embodiment of the present disclosure.

FIG. 6 includes an exploded perspective view and a sectional view illustrating disc-shaped sample detection plate 30 in Variation 2. FIG. 6 further includes an enlarged view illustrating sample container 32 provided in substrate 31. Sample detection plate 30 has a disc shape similar to an optical disk such as a CD or a DVD, and has circular hole 34 at its center. Sample detection plate 30 includes substrate 31, sample container 32 provided in substrate 31, and substrate 33 provided so as to cover sample container 32. Substrate 31 contains a first material that emits autofluorescence in response to electromagnetic waves having a predetermined wavelength. Incidentally, although sample container 32 is circular when viewed from above, there is no particular limitation to this.

Substrate 31 includes base material 31a and sample containing layer 31b. Sample containing layer 31b is a layer in which sample container 32 is formed. Sample containing layer 31b is formed of a resin, for example. Sample containing layer 31b is joined to an upper surface of base material 31a by an adhesive or the like. The first material that emits autofluorescence 9A is contained in base material 31a. It should be noted that the first material may be contained in sample containing layer 31b or in both base material 31a and sample containing layer 31b. By allowing sample detection plate 30 to have a disc shape as described above, it is possible to detect the sample using a detection device having a configuration similar to a known optical pickup device. The known optical pickup device is a device used for playback of a CD, a DVD, and a Blu-ray disc. In sample detection plate 30, when the optical pickup device including the fluorescent optical system is located above substrate 31, the light receiver receives autofluorescence emitted by substrate 31 in response to electromagnetic waves having a predetermined wavelength. Thus, it is appropriate that the intensity of autofluorescence emitted by substrate 33 should be less than that emitted by substrate 31. In other words, substrate 31 is formed of a first material that emits autofluorescence in response to electromagnetic waves emitted from a light source disposed on an upper surface side of substrate 33. Furthermore, it is appropriate that substrate 33 is formed of a second material that emits autofluorescence having a less intensity than an intensity of autofluorescence emitted by substrate 31 in response to electromagnetic waves having a predetermined wavelength.

Figure 7:
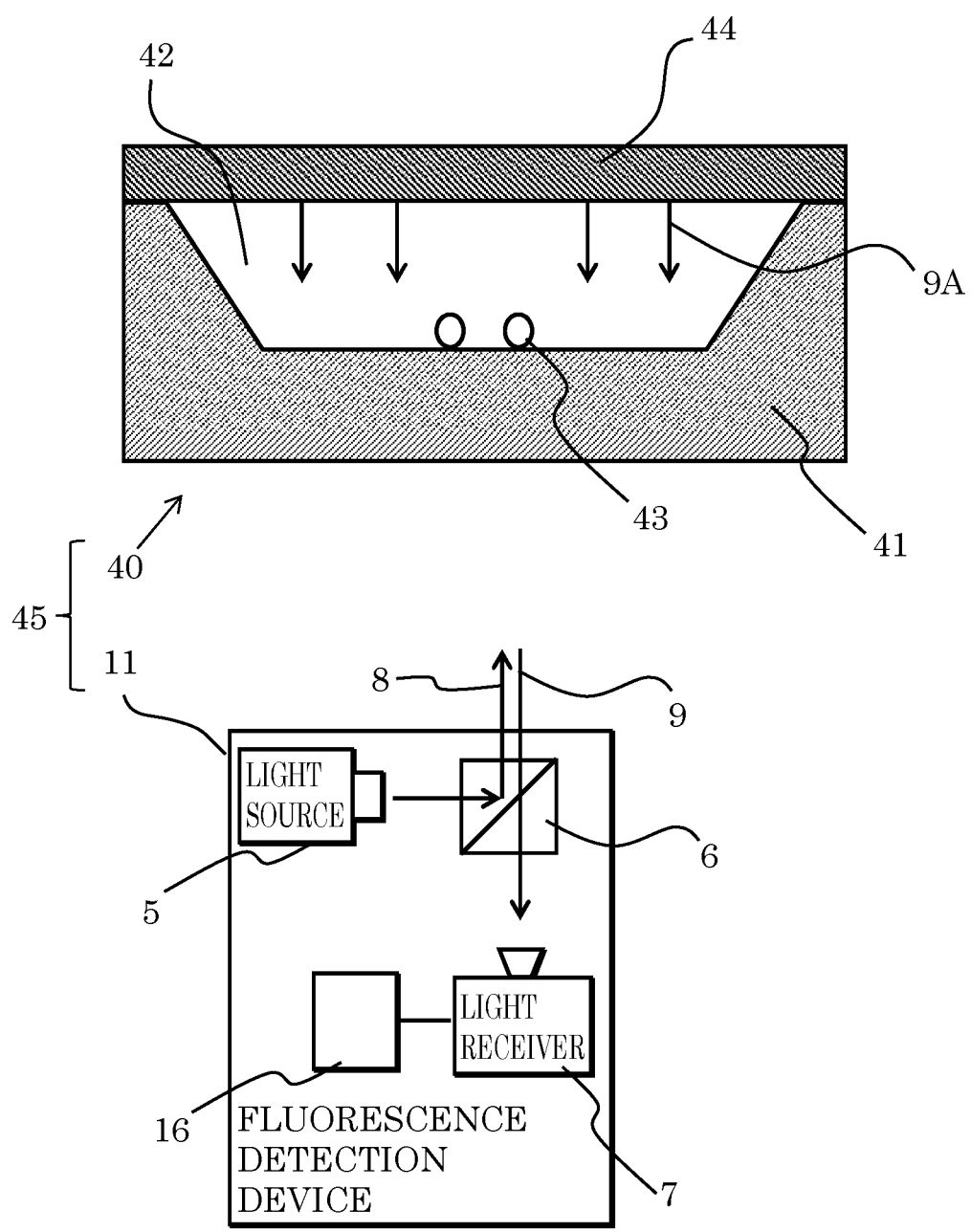
FIG. 7 is a sectional view schematically illustrating another sample detection plate in an embodiment of the present disclosure.

FIG. 7 illustrates fluorescence detection system 45 in Variation 3. Fluorescence detection system 45 is different from fluorescence detection system 15 in that fluorescence detection device 11 is disposed below a lower surface of substrate 41 of sample detection plate 40. In this case, electromagnetic waves 8 emitted from light source 5 pass through sample container 42 and reach substrate 44. Then, light receiver 7 receives autofluorescence 9A emitted by substrate 44. Thus, in sample detection plate 40, substrate 44 is formed of a first material that emits autofluorescence 9A in response to electromagnetic waves 8 having a predetermined wavelength. It is appropriate that substrate 41 should be formed of a second material that emits autofluorescence having a less intensity than an intensity of autofluorescence emitted by the first material in response to electromagnetic waves 8 having a predetermined wavelength. Sample container 42 in which sample 43 that absorbs electromagnetic waves having a predetermined wavelength is to be contained is provided on an upper surface of substrate 41. Substrate 44 is disposed facing substrate 41 so as to cover sample container 42. In other words, sample container 42 is provided on a lower surface of substrate 44. Autofluorescence 9A emitted by substrate 44 in response to electromagnetic waves 8 having a predetermined wavelength passes through sample container 42 and is detected by light receiver 7. In other words, substrate 44 has a function of first substrate 1 illustrated in FIG. 2. Additionally, substrate 41 has a function of second substrate 4 illustrated in FIG. 2.

With such a configuration, fluorescence detection device 11 including the fluorescent optical system detects autofluorescence 9A emitted by substrate 44 in response to electromagnetic waves 8 with which sample detection plate 40 is irradiated, thereby detecting the outer shape of the cells.

Moreover, by staining a protein or a nucleus in sample 43 with fluorochrome, it is possible to fluorescently detect cells at the same time.

It should be noted that a position of light source 5 is not limited to the lower surface side of substrate 41 of sample detection plate 40. For example, light source 5 may be disposed on an upper surface side or a lateral surface side of substrate 41.

Likewise, in sample detection plate 30, when the optical pickup device including the fluorescent optical system is located below substrate 31, light receiver 7 receives autofluorescence emitted by substrate 33 in response to electromagnetic waves having a predetermined wavelength. Thus, it is appropriate that the intensity of autofluorescence emitted by substrate 31 should be less than that emitted by substrate 33. In other words, substrate 33 is formed of a first material that emits autofluorescence in response to electromagnetic waves emitted from a light source disposed on the lower surface side of substrate 31. Furthermore, it is appropriate that substrate 31 is formed of a second material that emits autofluorescence having a less intensity than an intensity of autofluorescence emitted by substrate 33 in response to electromagnetic waves having a predetermined wavelength. The same applies to sample detection plate 20. In other words, substrate 33 has a function of first substrate 1 illustrated in FIG. 2. Substrates 21 and 31 have a function of second substrate 4 illustrated in FIG. 2.

Using the sample detection plate disclosed herein allows the detection device to obtain a captured image with a sharp outline of the sample. Accordingly, by image processing of the captured image, it is possible to detect the outer shape of the sample, thereby easily determining the size and number of the samples in the observation image.

In a sample including plural kinds of biomaterials that are mixed together, at least one kind of the biomaterials in the sample is fluorescently-labeled to emit fluorescence specifically, making it possible to not only detect the outer shape of the cells but also easily distinguish between the mixed biomaterials in the sample. For example, a sample including plasmodia having cell nucleuses and red blood cells having no cell nucleus that are mixed together is labeled with DAPI or SYTO40, which is a nucleic acid stain, so that the plasmodia alone specifically emit fluorescence in the sample. This sample is fluorescently observed using the sample detection plate according to the present disclosure, whereby the plasmodia are detected as bright spots and the red blood cells are detected as dark outer shapes. In this case, it is appropriate to select fluorochrome and a substrate material so that the intensity of autofluorescence emitted by the substrate is less than the intensity of the bright spots of the plasmodia. More specifically, it is beneficial that the intensity of the fluorescently bright spots should be at least twice as much as the intensity of the autofluorescence emitted by the substrate. The fluorochrome and the substrate material are determined using as indicators a quantum yield and a fluorescence wavelength of each material and a detection efficiency in the optical system. This makes it possible to identify a part brighter than the autofluorescence intensity in the substrate as the plasmodia and a part darker than the same as the red blood cells in the fluorescent image to be observed.

Furthermore, the kinds of the biomaterials or the fluorochrome are not limited to the above-noted combination. For example, a sample including red blood cells and reticulocytes that are mixed together may be used. In this case, using SYTO40 that stains nucleic acids present only in the reticulocytes makes it possible to identify the reticulocytes as the fluorescently bright spots.

Moreover, the above-mentioned sample is not necessarily limited to the biomaterial but may be an organic compound or an inorganic substance.

Incidentally, the method of detecting the outer shape of cells using the fluorescent optical system can include a method of staining a cell membrane with fluorochrome. However, this method requires a process of staining the cell membrane, complicating the operation. In contrast, when using sample detection plate 10 disclosed herein, it is not necessary to stain the cell membrane with fluorochrome, so that the outer shape of the cells can be detected with a simple operation. Also, the cells are not damaged by the fluorochrome.

In the present disclosure, terms indicating directions such as the "upper surface," "lower surface," "above," "below" and so on indicate relative directions that depend only on a positional relationship between structural components of the sample detection plate, and do not indicate absolute directions such as a vertical direction.

Although the sample detection plates according to one or more aspects have been described based on the embodiment above, the present disclosure is not limited to this embodiment. As long as not departing from the purport of the present disclosure, many variations of the above embodiment conceivable by a person skilled in the art and modes configured by the combination of the structural components in different embodiments may be included in the scope of one or more aspects of the present disclosure.

Although only an exemplary embodiment of the present disclosure has been described in detail above, those skilled in the art will readily appreciate that many modifications are possible in the exemplary embodiment without materially departing from the novel teachings and advantages of the present disclosure. Accordingly, all such modifications are intended to be included within the scope of the present disclosure.

INDUSTRIAL APPLICABILITY

The present disclosure uses the detection device including the fluorescent optical system to detect autofluorescence emitted by the first substrate in response to electromagnetic waves with which sample detection plate is irradiated, thereby detecting the outer shape of the samples. Thus, it is possible to easily determine the size, number, density, etc. of the samples.

What is claimed is:

1. A sample detection plate comprising:
   a first substrate having a first surface;
   a second substrate that is disposed facing the first surface of the first substrate; and
   a sample container that is provided on the first surface of the first substrate to contain a sample that absorbs electromagnetic waves having a predetermined wavelength, wherein:
   the first substrate includes a first material that emits autofluorescence in response to the electromagnetic waves having the predetermined wavelength,
   the sample container is sandwiched between the first substrate and the second substrate,
   the second substrate includes a second material that emits autofluorescence in response to the electromagnetic waves having the predetermined wavelength, and
   the autofluorescence emitted by the second material has a less intensity than an intensity of the autofluorescence emitted by the first substrate.

2. The sample detection plate according to claim 1, wherein the second substrate comprises a transparent material.

3. The sample detection plate according to claim 1, wherein the first material comprises polycarbonate.

4. The sample detection plate according to claim 1, wherein the sample container is defined by a recess formed in the first substrate.

5. The sample detection plate according to claim 1, wherein the sample container is defined by a recess formed in the second substrate.

6. The sample detection plate according to claim 1, wherein the sample container comprises a plurality of sample containers.

7. A fluorescence detection system comprising:
the sample detection plate according to claim 1; and
a fluorescence detection device,
wherein the fluorescence detection device includes:
a light source that emits the electromagnetic waves having the predetermined wavelength from a first surface side of the first substrate;
a light receiver that is disposed on the first surface side of the first substrate and receives through the sample container the autofluorescence emitted by the first substrate when the first substrate is irradiated with the electromagnetic waves having the predetermined wavelength; and
an image generator that generates an image using the autofluorescence received by the light receiver.

8. A fluorescence detection method using a sample detection plate that includes a first substrate having a first surface, and a sample container that is provided on the first surface of the first substrate to contain a sample that absorbs electromagnetic waves having a predetermined wavelength, wherein the first substrate includes a first material that emits autofluorescence in response to the electromagnetic waves having the predetermined wavelength,
the method comprising:
placing the sample in the sample container;
passing the electromagnetic waves having the predetermined wavelength through the sample container from a first surface side of the first substrate to irradiate the first substrate with the electromagnetic waves having the predetermined wavelength;
receiving the autofluorescence from the first surface side of the first substrate through the sample container, the autofluorescence being emitted by the first substrate in response to the electromagnetic waves; and
generating an image using the autofluorescence emitted by the first substrate and received through the sample container, wherein:
in the placing, the sample is stained with fluorochrome that emits fluorescence in response to the electromagnetic waves having the predetermined wavelength,
in the placing, the sample is placed in the sample container together with a solution,
the solution contains the fluorochrome, and
the fluorescence emitted by the fluorochrome has a greater intensity than an intensity of the autofluorescence emitted by the first substrate.

9. The fluorescence detection method according to claim 8,
wherein the sample is a red blood cell, and
the predetermined wavelength is in a range from 400 nm to 450 nm.

10. The fluorescence detection method according to claim 8,
wherein, in the image that has been generated, a region where the intensity is less than or equal to a predetermined threshold is determined to be a sample region, and a region where the intensity is greater than the predetermined threshold is determined to be a background region.

* * * * *